United States Patent
Hebrank et al.

(10) Patent No.: US 8,235,003 B2
(45) Date of Patent: Aug. 7, 2012

(54) METHODS AND APPARATUS FOR IDENTIFYING LIVE EGGS

(75) Inventors: John H. Hebrank, Durham, NC (US); Thomas Bryan, Raleigh, NC (US); Paul Brandford, Cheshire (GB)

(73) Assignee: Embrex, Inc., Durham, NC (US)

( * ) Notice: Subject to any disclaimer, the term of this patent is extended or adjusted under 35 U.S.C. 154(b) by 0 days.

(21) Appl. No.: 11/492,720

(22) Filed: Jul. 25, 2006

(65) Prior Publication Data

US 2007/0024844 A1 Feb. 1, 2007

Related U.S. Application Data

(60) Provisional application No. 60/703,845, filed on Jul. 29, 2005.

(51) Int. Cl.
*A01K 45/00* (2006.01)

(52) U.S. Cl. ........................................ 119/6.8
(58) Field of Classification Search ............... 119/6.8
See application file for complete search history.

(56) References Cited

U.S. PATENT DOCUMENTS

| | | | |
|---|---|---|---|
| 4,458,630 A | 7/1984 | Sharma et al. | |
| 4,591,723 A | 5/1986 | Akiyama | |
| 4,681,063 A | 7/1987 | Hebrank | |
| 4,914,672 A | 4/1990 | Hebrank | |
| 4,955,728 A | 9/1990 | Hebrank | |
| 5,017,003 A | 5/1991 | Keromnes et al. | |
| 5,028,421 A | 7/1991 | Fredericksen et al. | |
| 5,158,038 A | 10/1992 | Sheeks et al. | |
| 5,173,737 A | 12/1992 | Mitchell et al. | |
| 5,745,228 A | 4/1998 | Hebrank et al. | |
| 5,900,929 A | 5/1999 | Hebrank et al. | |
| 6,145,668 A | 11/2000 | DePauw et al. | |
| 6,149,375 A | 11/2000 | Hebrank | |
| 6,213,709 B1 | 4/2001 | Hebrank | |
| 6,224,316 B1 | 5/2001 | Hebrank et al. | |
| 6,750,954 B2 | 6/2004 | Hebrank et al. | |
| 7,237,505 B2 * | 7/2007 | Cantrell et al. | 119/6.8 |
| 2003/0185422 A1 * | 10/2003 | Taniguchi | 382/110 |

FOREIGN PATENT DOCUMENTS

WO WO 02/086495 A2 10/2002
WO WO 03/104797 A1 12/2003

OTHER PUBLICATIONS

International Search Report and Written Opinion of the International Searching Authority, corresponding to PCT/US2006/029023, mailed Apr. 25, 2007.
European Search Report dated Jun. 4, 2009; Application No./Patent No. 06788555.8-1240 / 1910818 PCT/US2006029023.

* cited by examiner

*Primary Examiner* — Monica Williams
(74) *Attorney, Agent, or Firm* — Barbara L. Renda; Scott C. Mayhew (57) ABSTRACT

Egg candling methods and apparatus are provided wherein black rot eggs can be identified and removed. A method of identifying live eggs includes illuminating eggs in a carrier with light from a light source; receiving light passing through each egg at a light detector; generating an output signal that corresponds to light received at a light detector for each respective egg; analyzing the output signal for each egg to determine opacity of each egg; removing eggs having an opacity less than a first opacity value; and removing eggs having an opacity greater than a second opacity value that is different from the first opacity value.

24 Claims, 6 Drawing Sheets

METHODS AND APPARATUS FOR IDENTIFYING LIVE EGGS

RELATED APPLICATION

This application claims the benefit of and priority to U.S. Provisional Patent Application No. 60/703,845, filed Jul. 29, 2005, the disclosure of which is incorporated herein by reference as if set forth in its entirety.

FIELD OF THE INVENTION

The present invention relates generally to eggs and, more particularly, to methods and apparatus for processing eggs.

BACKGROUND OF THE INVENTION

Discrimination between poultry eggs on the basis of some observable quality is a well-known and long-used practice in the poultry industry. "Candling" is a common name for one such technique, a term which has its roots in the original practice of inspecting an egg using the light from a candle. As is known to those familiar with eggs, although egg shells appear opaque under most lighting conditions, they are in reality somewhat translucent, and when placed in front of direct light, the contents of the egg can be observed.

An egg is referred to as a "live" egg if it has a viable embryo. An egg is referred to as "clear" or "infertile" if it does not have an embryo. More particularly, a "clear" egg is an infertile egg that has not rotted. An egg is referred to as "early dead" if it has an embryo which died at about one to five days old. An egg is referred to as "mid-dead" if it has an embryo which died at about five to fifteen days old. An egg is referred to as "late-dead" if it has an embryo which died at about fifteen to eighteen days old. An egg is referred to as "rotted" if it includes a rotted infertile yolk (for example, as a result of a crack in the egg's shell) or, alternatively, a rotted, dead embryo.

Eggs which are to be hatched to live poultry are typically candled during embryonic development to identify clear, rotted, and dead eggs (collectively referred to as "non-live eggs"). Non-live eggs are typically removed from incubation to increase available incubator space. In many instances it is desirable to introduce a substance, via in ovo injection, into a live egg prior to hatch. Injections of various substances into avian eggs are typically employed in the commercial poultry industry to decrease post-hatch mortality rates or increase growth rates of hatched birds. Examples of substances that have been used for, or proposed for, in ovo injection include vaccines, antibiotics and vitamins. Examples of in ovo treatment substances and methods of in ovo injection are described in U.S. Pat. No. 4,458,630 to Sharma et al. and U.S. Pat. No. 5,028,421 to Fredericksen et al.

In ovo injections of substances typically occur by piercing an egg shell to create a hole therethrough (e.g., using a punch or drill), extending an injection needle through the hole and into the interior of the egg (and in some cases into the avian embryo contained therein), and injecting one or more treatment substances through the needle. An example of an in ovo injection device is disclosed in U.S. Pat. No. 4,681,063 to Hebrank. This device positions an egg and an injection needle in a fixed relationship to each other, and is designed for high-speed automated injection of a plurality of eggs. The selection of both the site and time of injection treatment can impact the effectiveness of the injected substance, as well as the mortality rate of the injected eggs or treated embryos. See, for example, U.S. Pat. No. 4,458,630 to Sharma et al., U.S. Pat. No. 4,681,063 to Hebrank, and U.S. Pat. No. 5,158,038 to Sheeks et al.

In commercial poultry production, only about 60% to 90% of commercial broiler eggs hatch. Eggs that do not hatch include eggs that were not fertilized, as well as fertilized eggs that have died. Infertile eggs may comprise from about 5% up to about 25% of all eggs in a set. Due to the number of non-live eggs encountered in commercial poultry production, the increasing use of automated methods for in ovo injection, and the cost of treatment substances, an automated method for accurately identifying live eggs and selectively injecting only live eggs, is desirable.

There are other applications where it is important to be able to identify live and non-live eggs. One of these applications is the cultivation and harvesting of vaccines in live eggs (referred to as "vaccine production eggs"). For example, human flu vaccine production is accomplished by injecting seed virus into a chicken egg at about day eleven of embryonic development (Day-11 egg), allowing the virus to grow for about two days, euthanizing the embryo (typically by cooling the egg), and then harvesting the amniotic fluid from the egg. Typically, eggs are candled before injection of a seed virus to facilitate removal of non-live eggs. Vaccine production eggs may be candled one or more days prior to injection of a seed virus therein. Identification of live eggs in vaccine production is important because it is desirable to prevent seed vaccine from being wasted in non-live eggs and to reduce costs associated with transporting and disposing of non-live eggs. Furthermore, eggs that contain dead embryos are especially a concern since they may have been killed by bacterial or microbial organisms that could further contaminate the vaccine production process either at the injection of the seed material or at harvest. Contaminated eggs may be called "rots" related to the transformation of the embryo or egg material into a custard-like material that may smell like rotten eggs.

U.S. Pat. Nos. 4,955,728 and 4,914,672, both to Hebrank, describe a candling apparatus that uses infrared detectors and the infrared radiation emitted from an egg to distinguish live from infertile eggs. U.S. Pat. No. 5,745,228 to Hebrank et al. describes a candling apparatus that includes a photodetector and a photoemitter that are configured to be positioned on opposite sides of an egg. Light is generated in short bursts from each photoemitter and the corresponding photodetector only monitors while it's corresponding photoemitter is operational. A flat of eggs is continuously "scanned" as it moves through the candling apparatus with each detector-source pair active only while at least adjacent, and preferably all other, pairs are quiescent.

A conventional candling apparatus typically identifies eggs to be removed from a flat when opacity is less than a fixed light level. This fixed light level allows clear eggs, early dead eggs and mid dead eggs to be identified and removed. Unfortunately, some non-live eggs, referred to as "black rot" eggs, can be difficult to detect via conventional candling methods. Black rot eggs, which are believed to be related to poor shell quality and/or small shell cracks, are believed to contain bacterial contamination that has caused the interior to have a dark or blackened appearance. Black rot eggs can contaminate egg processing equipment, particularly in ovo injection equipment utilized to inoculate egg embryos and in ovo equipment utilized in vaccine production. Accordingly, a need exists to more accurately detect black rot eggs so that they can be removed, while also reducing the number of live eggs that are mistakenly identified as non-live.

SUMMARY OF THE INVENTION

In view of the above discussion, egg candling methods and apparatus are provided wherein black rot eggs can be identified and removed. According to some embodiments of the present invention, a method of identifying live eggs includes illuminating eggs in a carrier with light from a light source; receiving light passing through each egg at a light detector (e.g., photodetector, video camera, etc.); generating an output signal that corresponds to light received at a light detector for each respective egg; analyzing the output signal for each egg to determine opacity of each egg; removing eggs having an opacity less than a first opacity value; and removing eggs having an opacity greater than a second opacity value that is different from the first opacity value. Removed eggs may be discarded or may be subjected to additional processing for various purposes.

According to some embodiments of the present invention, a seed virus (or multiple seed viruses) may be injected into each egg identified as containing a live embryo (i.e., eggs having an opacity between the first and second opacity values). For example, a human flu virus may be injected into each egg identified as containing a live embryo.

According to some embodiments of the present invention an apparatus that identifies live eggs includes a candler that candles eggs within a carrier. The candler includes a light source that illuminates each egg within a carrier with light; a detector that receives light passing through each egg from the light source and that generates an output signal corresponding to the received light; and a processor in communication with the candler that analyzes the output signal for each egg to determine opacity of each egg. The processor designates an egg to be non-live if opacity is less than a first opacity value, and wherein the processor designates an egg to be non-live if opacity is greater than a second opacity value that is different from the first opacity value.

According to some embodiments of the present invention, the apparatus includes an egg removal device that removes eggs (e.g., non-live eggs) from the carrier.

According to some embodiments of the present invention, the apparatus includes a backfill station that replaces eggs removed from the carrier with other eggs.

According to some embodiments of the present invention, the apparatus includes an injection device configured to inject a substance (e.g., an inoculation, virus, etc.) into each live egg.

DETAILED DESCRIPTION OF THE INVENTION

The present invention now is described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise. All publications, patent applications, patents, and other references mentioned herein are incorporated herein by reference in their entireties.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/ or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a "first" element, component, region, layer or section discussed below could also be termed a "second" element, component, region, layer or section without departing from the teachings of the present invention. The sequence of operations (or steps) is not limited to the order presented in the claims or figures unless specifically indicated otherwise.

Eggs at Day 11 of incubation ("Day 11 eggs") are desirable for use in vaccine production (e.g., human flu vaccine production). Applicants have unexpectedly discovered that black rot eggs, which appear to originate from a few flocks, are more opaque (i.e., have a lower light value) than Day 11 live eggs. More specifically, Applicants have discovered that between about forty percent and eighty percent (40%-80%) of all rotten eggs have light values less than about ninety nine percent (99%) of live Day 11 eggs. Accordingly, Applicants have established a candling procedure for Day 11 eggs wherein two cutoff levels are set. Eggs having an opacity less than a first light level (i.e., first cutoff) are removed and eggs having an opacity greater than a second light level (i.e., second cutoff) are removed. This is illustrated in FIG. 1.

Figure 1:
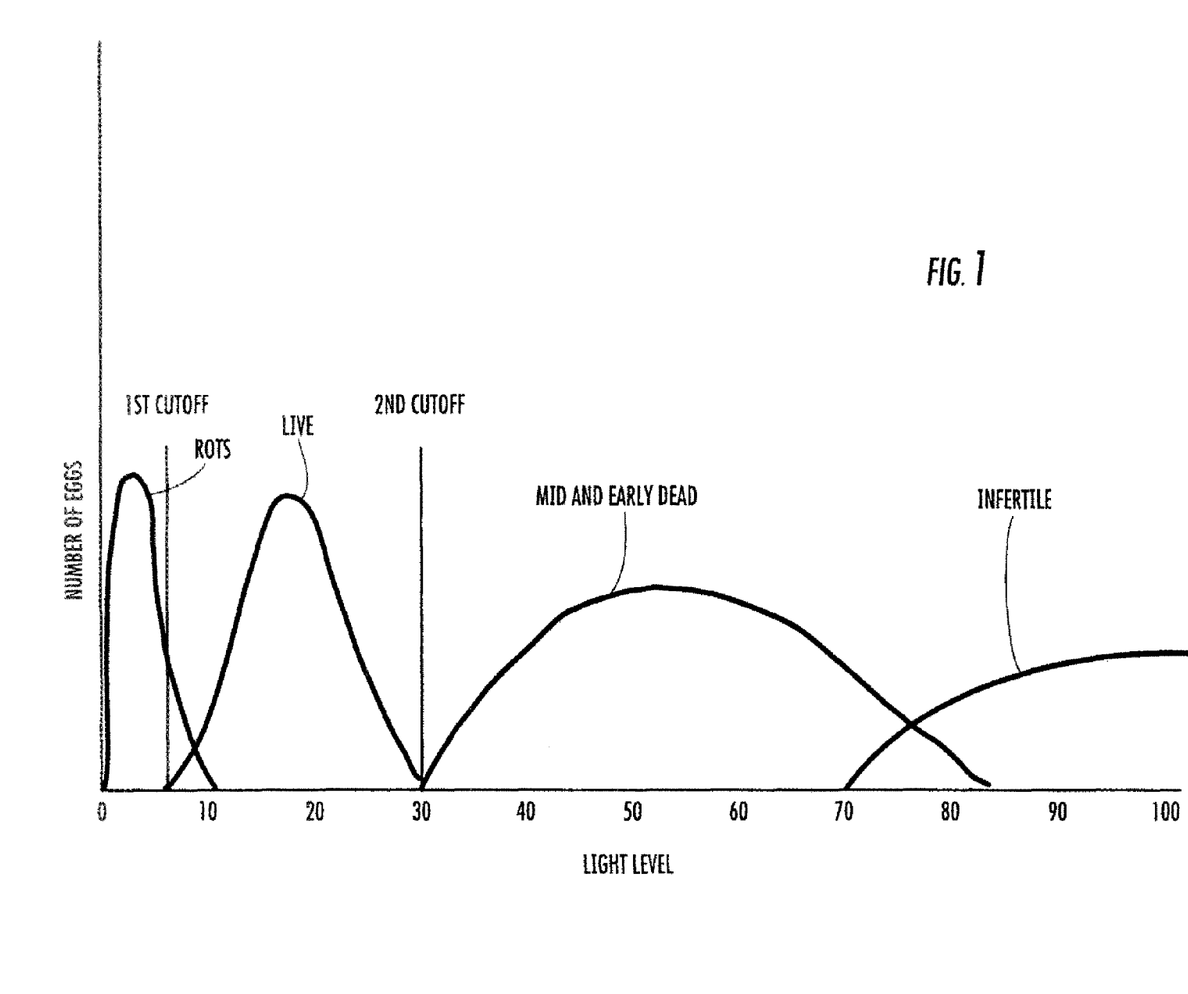
FIG. 1 is a graph that illustrates opacity levels for various types of eggs and that illustrates first and second light level cutoffs that facilitate live egg identification, according to some embodiments of the present invention.

The light level values illustrated in FIG. 1 are generated by the S Beam light candling system of the Vaccine Saver™ vaccine delivery system available from Embrex, Inc. of Research Triangle Park, N.C. These light level values are unit-less and are values assigned by the S beam light candling system. However, these light values are linear and correlate directly to the amount of light passing through an egg during candling, so that twice as much light doubles the measured value. Embodiments of the present invention can be implemented using any candling apparatus that generates light or opacity levels when candling eggs. In order to use this technique with another linear opacity measurement system, a large group of eggs would be hand candled and marked as live, infertile, dead and rotten. These eggs would be run through the opacity measurement system and light values recorded for each type of egg. The lower and upper cutoffs would then be determined by a criteria such as minimizing the percentage of live eggs discarded or maximizing the number of dead eggs retained.

In FIG. 1, light levels passing through eggs via a candling apparatus is plotted along the "X" axis and the number of candled eggs is plotted along the "Y" axis. As illustrated, rotten eggs, including black rot eggs, generally fall within a distribution that has an opacity level upper end of about 10. Live eggs generally fall within a distribution that has an opacity level lower end of about 6 and an upper end of about 30 (for the S Beam light candling system). Middle and early dead eggs generally fall within a distribution that has an opacity level lower end of about 30 and an upper end of about 80. Infertile eggs generally fall within a distribution that has an opacity level lower end of about 70 and an upper end in excess of 100. Thus, according to some embodiments of the present invention illustrated via FIG. 1, all eggs with opacity levels less than 6 will be removed and all eggs with opacity levels greater than 30 will be removed. In other words, the first opacity value is 6 and the second opacity value is 30 and these opacity values represent the first and second cutoffs, respectively.

Figure 2:
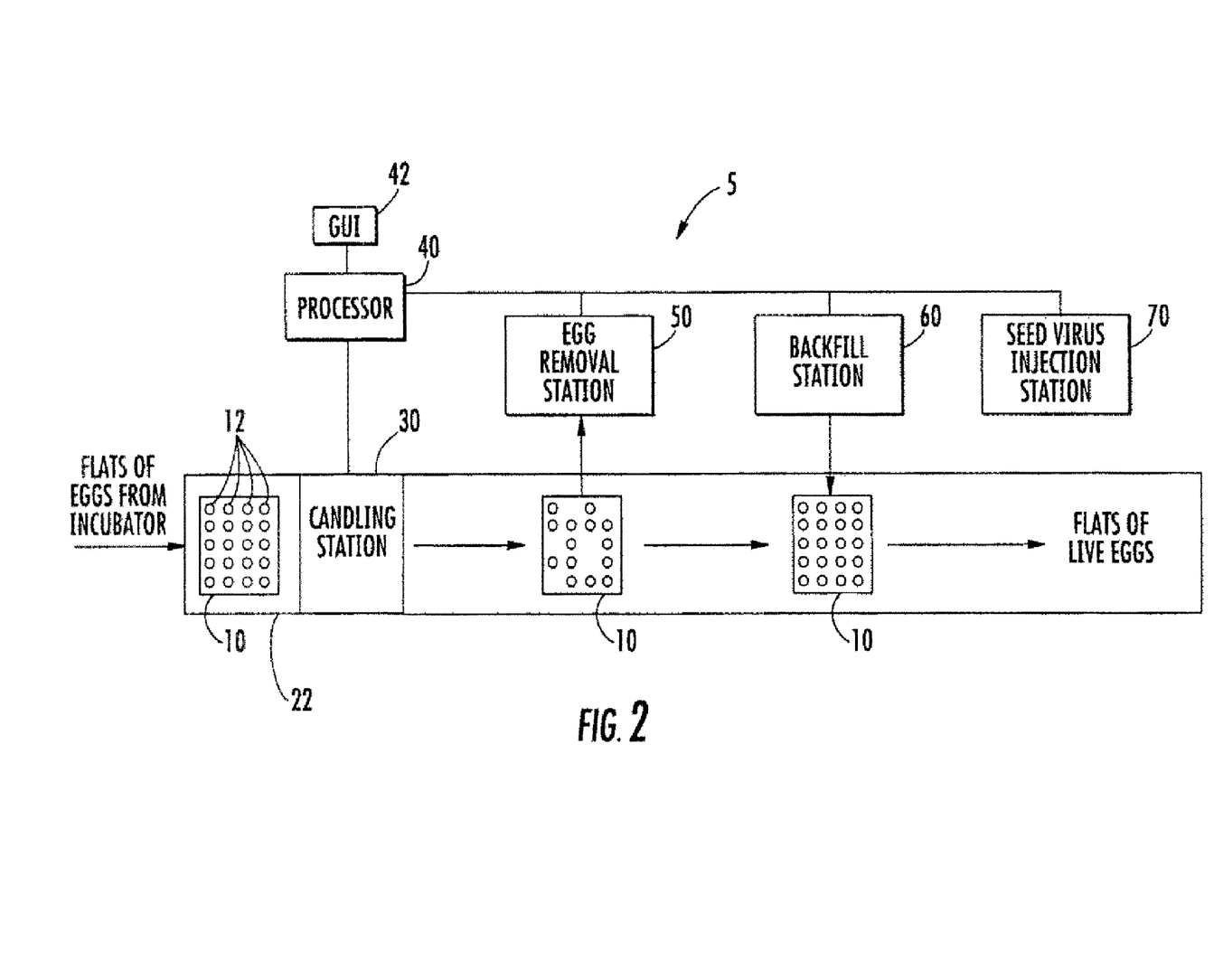
FIG. 2 is a block diagram of an apparatus that identifies live and non-live eggs, according to some embodiments of the present invention.

FIG. 2 is a block diagram of an egg processing system 5 that is configured to identify eggs having an opacity value less than a first opacity value (the first cutoff) and eggs having an opacity value greater than a second opacity value (the second cutoff) that is different from the first opacity value, according to some embodiments of the present invention. The illustrated system 5 is utilized for the production of human flu vaccine and includes a candling station 30, egg removal station 50, backfill station 60 and seed virus injection station 70. A processor 40 (e.g., a personal computer or other computing device) controls operations of each of the candling station 30, egg removal station 50, backfill station 60 and seed virus injection station 70. An operator interface (e.g., a display, graphical user interface, etc.) 42 may be provided that is configured to allow an operator to interact with the processor 40 and the various stations (30,50,60,70).

In the illustrated embodiment, a carrier (e.g., an egg flat) 10 of eggs 12 is conveyed via a conveyor 22 to a candling station 30 that is configured to determine the opacity of each egg and to designate each egg 12 within the flat 10 as being either live or non-live. Any type of conveying system suitable for conveying flats (or other carriers) of eggs may be utilized in accordance with embodiments of the present invention. Egg conveying systems are well known to those of skill in the art and need not be described further herein.

Although eggs conventionally are carried in egg flats, any means of presenting a plurality of eggs over time to a candling station 30, as well as to other egg processing equipment, may be used. Egg flats of virtually any type may be used in accordance with embodiments of the present invention. Flats may contain any number of rows, such as seven rows of eggs, with rows of six and seven being most common. Moreover, eggs in adjacent rows may be parallel to one another, as in a "rectangular" flat, or may be in a staggered relationship, as in an "offset" flat. Examples of suitable commercial flats include, but are not limited to, the "CHICKMASTER 54" flat, the "JAMESWAY 42" flat and the "JAMESWAY 84" flat (in each case, the number indicates the number of eggs carried by the flat). Egg flats are well known to those of skill in the art and need not be described further herein.

The candling station 30 includes a light source that illuminates each egg within a carrier with light and a detector that receives light passing through each egg from the light source and that generates an output signal that corresponds to received light, as will be described below. An exemplary light candling system that may be utilized in accordance with embodiments of the present invention is described in U.S. Pat. No. 5,745,228 to Hebrank et al. A suitable commercial light candling system includes the S Beam light candling system of the Vaccine Saver™ vaccine delivery system available from Embrex, Inc. of Research Triangle Park, N.C.

Figure 3:
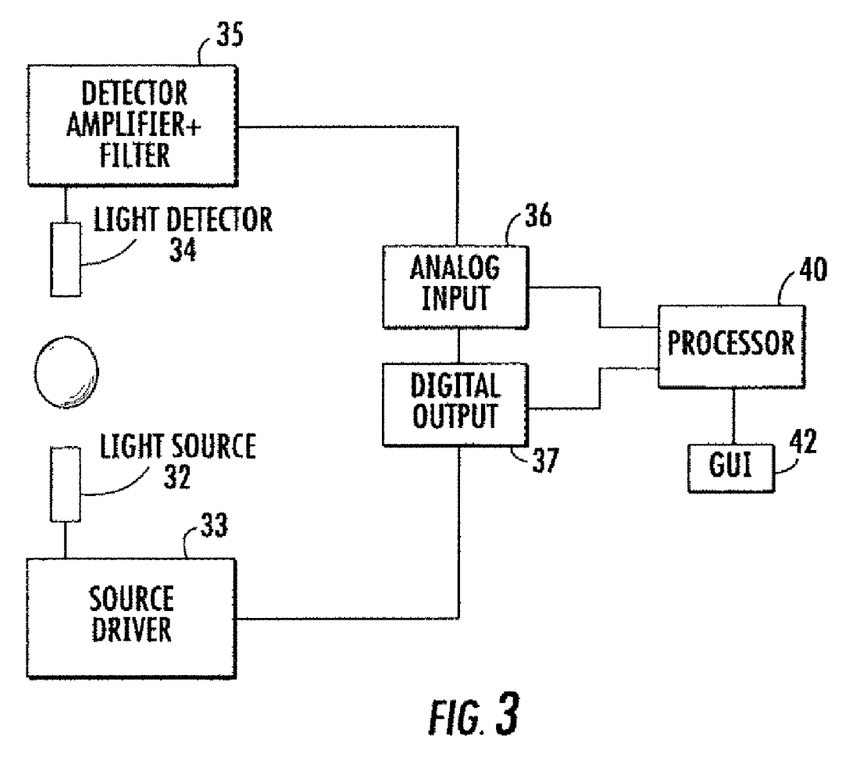
FIG. 3 is a block diagram of an exemplary light source and light detector pair from the candling station of FIG. 2, according to some embodiments of the present invention.

FIG. 3 illustrates an exemplary light source 32 and light detector 34 pair from the candling station 30 of FIG. 2. The candling station 30 contains a plurality of light source/light detector pairs to correspond with a row of eggs in a carrier, such as an egg flat. Each light source/light detector pair defines a respective optical channel. Each light detector 34 is associated with a detector amplifier and filter circuit 35, which is in turn associated with an analog input board 36. Each light source 32 (e.g., an infrared light source, a visible light source, etc.) is associated with a light source driver circuit 33, which is in turn associated with a digital output board 37. The light source 32 and light detector 34 in each pair are positioned on opposite sides of an egg, as would be understood by those skilled in the art. In FIG. 3, the light detector 34 is above and the light source 32 is below the egg, but these positions are not critical and could be reversed, or the light source and light detector may be placed in different orientations, so long as light from the light source illuminates the egg to the light detector.

Embodiments of the present invention are not limited to the illustrated orientation and configuration of the light source 32 and light detector 34. Moreover, embodiments of the present invention do not require that a respective light source (or sources) and detector be provided for each egg in a flat. Various numbers and combinations of light sources and detectors may be utilized without limitation.

Although the illustrated embodiment implements a light detector as a photodetector, according to some embodiments of the present invention, a camera may be used with the light value based upon the outputs of a single, or group of, pixels. According to some embodiments of the present invention, use of a camera (e.g., a video camera, etc.) may allow measurement of multiple eggs. For example, a plurality of eggs in a carrier may be candled substantially simultaneously via a video camera.

The input and output boards 36, 37 may physically be one or more separate boards and are associated with processor 40, with operation of the system monitored on a user interface 42 associated with the processor. In operation, light is generated in short bursts from each light source 32 (e.g., 50 to 300 microseconds) and the corresponding light detector 34 monitors while its corresponding light source 32 is operational. To reduce the effect of ambient light, the output of a light detector 34 when no light is on is subtracted from the reading when the light is on. A flat of eggs is continuously "scanned" as it moves through the candling apparatus 30 with each light detector/light source pair active while at least adjacent, and preferably all other, light detector/light source pairs are quiescent.

According to some embodiments of the present invention, the processor 40 analyzes output signals from each detector 34 and stores information received from the candling station 30 about each egg 12. The processor 40 is also configured to determine whether an egg has an opacity value less than the first cutoff or an opacity value greater than the second cutoff, as described above.

Embodiments of the present invention are not limited to the configuration of FIG. 2 and the processor 40 is not required to control all of the illustrated components. According to alternative embodiments of the present invention, one or more of the stations (30,50,60,70) described with respect to FIG. 2 may be controlled by individual programmable logic controllers (PLCs). Data may be transferred back and forth from a PLC to a central computer database controller for storage. For example, a central database may be provided to store information about eggs being processed. The central computer database controller may be configured to respond to individual PLCs when they request data or send data. The central computer database need not directly control the various stations under the control of respective PLCs.

In the illustrated apparatus 5, eggs 12 designated as non-live (i.e., eggs having opacity levels below the first cutoff and eggs having opacity levels above the second cutoff) are removed from the flat 10 downstream from the candling station 30 at egg removal station 50. According to some embodiments of the present invention, the processor 40 generates a selective removal signal for eggs determined to be non-live. The non-live eggs are removed from the flat 10 and discarded or used for some other purpose. A back fill station 60 may be utilized to place live eggs in empty positions created by removing non-live eggs.

The egg removal station 50 is configured to remove eggs identified as non-live. The processor 40 generates a selective removal signal for an egg 12 based upon whether the candling station 30 identified the egg 12 as being non-live. The egg removal station 50 may employ suction-type lifting devices as disclosed in U.S. Pat. No. 4,681,063 or in U.S. Pat. No. 5,017,003 to Keromnes et al., the disclosures of which are hereby incorporated by reference in their entireties. Various devices and methods for removing eggs may be utilized with embodiments of the present invention without limitation. Exemplary egg removal apparatus that may serve the function of the egg removal station 50 are described in U.S. Pat. Nos. 6,145,668; 6,149,375; 6,213,709; and 6,224,316, each of which is incorporated herein by reference in its entirety.

The egg removal station 50 preferably operates automatically and robotically. Alternatively, selected eggs may be identified on the user interface 42, optionally marked, and removed by hand.

In the illustrated embodiment of FIG. 2, a seed virus injection station 70 is provided downstream of the backfill station 60 and is operatively connected to the processor 40. The seed virus injection station 70 is configured to inject one or more seed viruses into each egg 12 within a flat 10 that is identified as containing a live embryo. An exemplary device for injecting a seed virus into a plurality of eggs in accordance with embodiments of the present invention is the INOVOJECT® automated injection system (Embrex, Inc., Research Triangle Park, N.C.). However, any in ovo injection device may be suitable for use according to embodiments of the present invention. Suitable injection devices preferably are designed to operate in conjunction with commercial egg carrier devices or flats.

Figure 4:
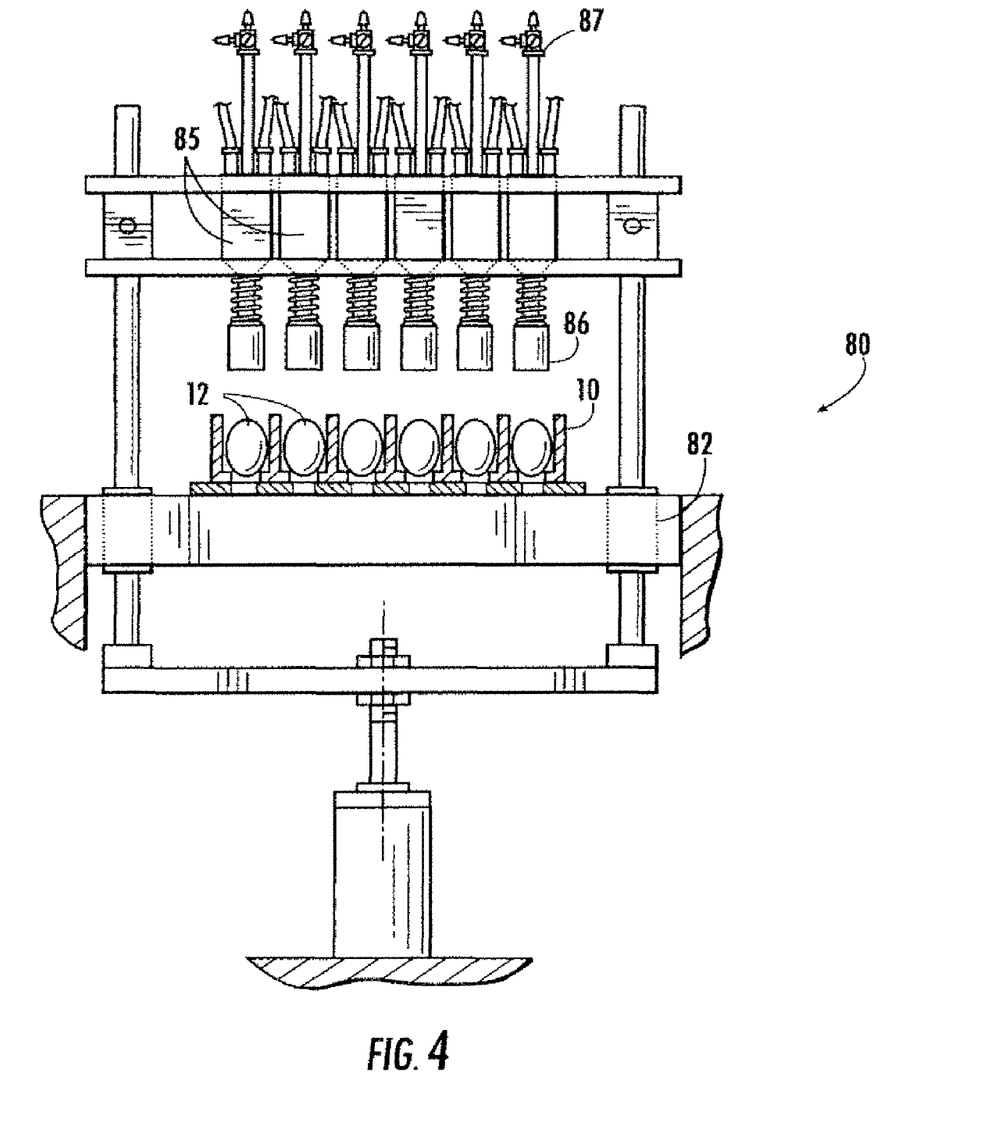
FIG. 4 is a side view of a multiple injection head in ovo injection/material removal device with which inoculation/ virus delivery devices and methods, as well as material removal devices and methods, according to some embodiments of the present invention may be used.

FIG. 4 illustrates an apparatus 80 that may be utilized to inject a seed virus into a plurality of eggs in ovo, as well as to remove material from a plurality of eggs, according to some embodiments of the present invention. The illustrated apparatus 80 includes a stationary base 82, and a plurality of injection delivery devices, or heads, 85 with fluid delivery means such as lumens or needle(s) positioned therein in accordance with known techniques. A flat 10 holds a plurality of eggs 12 in a substantially upright position. The flat 10 is configured to provide external access to predetermined areas of the eggs 12. Each egg 12 is held by the flat 10 so that a respective end thereof is in proper alignment relative to a corresponding one of the injection heads 85 as the injection head 85 advances towards the base 82 of the apparatus. However, in ovo injection (and in ovo material removal) devices may inject (or remove material from) eggs in various orientations. Embodiments of the present invention are not limited only to in ovo injection and/or removal devices that inject (or remove material from) eggs in the illustrated orientation.

Each of the plurality of injection heads 85 has opposing first and second ends 86, 87. The heads 85 have a first extended position and a second retracted position, as is known in the art. Upon extension of an injection head 85, the first end 86 is configured to contact and rest against predetermined areas of an external egg shell. When not injecting (or removing material from an egg), the injection heads 85 are retracted to rest a predetermined distance above the eggs 12 and stationary base 82. Alternatively, the base 82 can be longitudinally slidably moveable to position the eggs 12 in proper position relative to the injection heads 85.

After injection with a seed virus, the eggs 1 containing live embryos are transferred to an incubator 60 for a predetermined period of time.

At the end of this period of time, the eggs 1 are transferred to the vaccine harvesting station 70 where material from each egg 1 (e.g., amniotic fluid) is extracted. An exemplary device that may be adapted for use as a vaccine harvesting device in accordance with embodiments of the present invention is the INOVOJECT® automated injection system.

Figure 5:
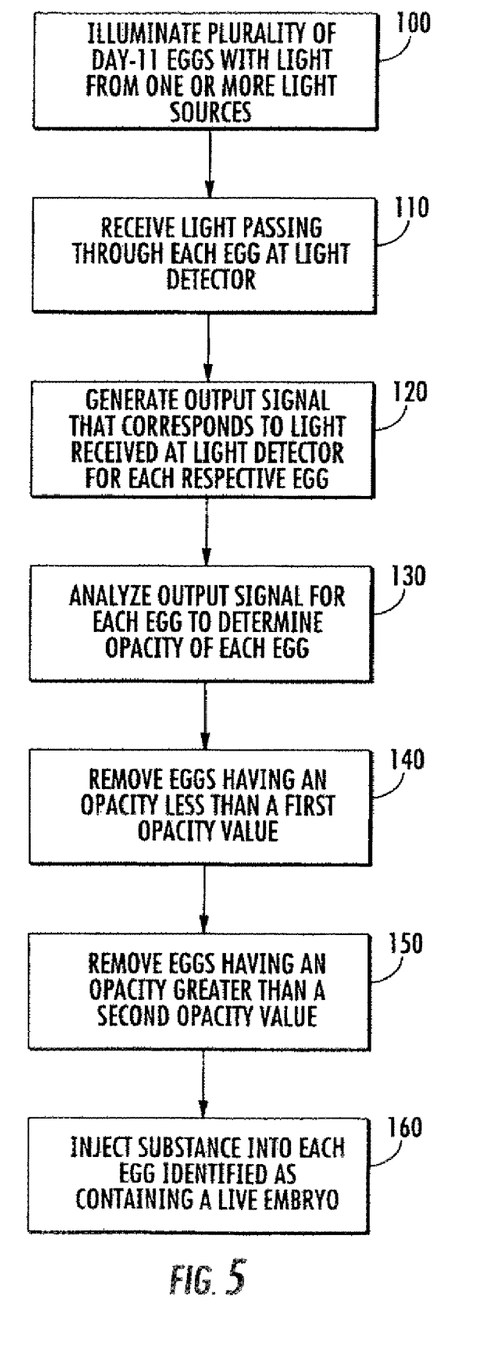
FIG. 5 is a flowchart of operations for identifying live eggs within a plurality of eggs, according to some embodiments of the present invention.
Figure 6:
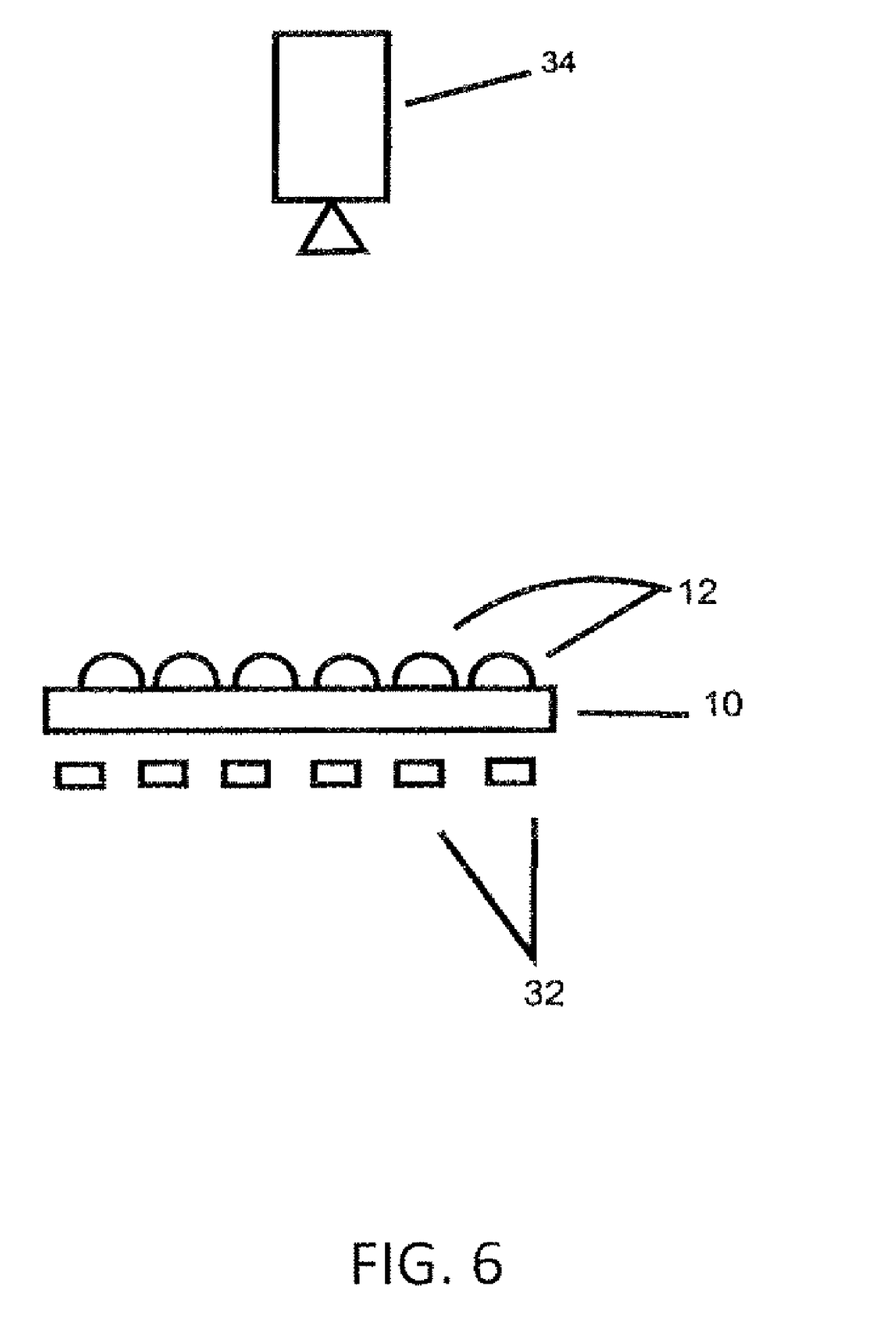
FIG. 6 is a side view of a flat of eggs (conveyed out of page) by the carrier, positioned between the light source (LEDS) that illuminate each egg, and the video camera that continuously reads the eggs as each row is illuminated.

Referring now to FIG. 5, a method of identifying live eggs within a plurality of eggs, according to some embodiments of the present invention, is illustrated. Each of a plurality of day-11 eggs is illuminated with light from one or more light sources (Block 100). Light passing through each egg is received at a light detector (Block 110). An output signal that corresponds to light received at a light detector is generated for each respective egg (Block 120). The output signal for each egg is analyzed to determine opacity of each egg (Block 130). Eggs having an opacity less than a first opacity value are removed (Block 140) and eggs having an opacity greater than a second opacity value that is different from the first opacity value are removed (Block 150). Removed eggs may be discarded or may be subjected to additional processing for various purposes. A substance may be injected into each egg identified as containing a live embryo (Block 160). For example, each egg identified as containing a live embryo can be inoculated with a treatment substance. Alternatively, a human flu virus may be injected into each egg identified as containing a live embryo.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed is:

1. A method of identifying live eggs, comprising:
   providing an egg opacity level distribution profile having a plurality of egg status distribution profiles indicative of egg viability at day eleven of incubation;
   providing an egg opacity level distribution profile having a rotten egg distribution profile, a live egg distribution profile, a dead egg distribution profile, and an infertile egg distribution profile,
   wherein each distribution profile corresponds to a different light level value;
   setting a first cutoff light level value and a second cutoff light level value according to the egg opacity level distribution profile such that eggs identified as having a light level value between the first and second cutoff light level values are designated as live egg;
   illuminating eggs in a carrier with light from a light source at day eleven of incubation;
   receiving light passing through each egg at a light detector;
   generating an output signal that corresponds to light received at a light detector for each respective egg;
   analyzing the output signal for each egg to determine a light level value of each egg;
   analyzing the light level value of each egg to determine the egg opacity level distribution profile;
   removing eggs having light level values less than the first cutoff light level value; and
   removing eggs having light level values greater than the second cutoff light level value, the second cutoff light level value being greater than the first cutoff light level value such that eggs analyzed as having light level values ranging between the first and second cutoff light level values are designated as live eggs and maintained in the carrier for injection.

2. The method of claim 1, wherein the light source and detector for each egg are positioned on respective opposite portions of the egg.

3. The method of claim 1, wherein the light source and detector for each egg are positioned on respective opposite end portions of the egg.

4. The method of claim 1, further comprising injecting a virus into each egg not removed from the carrier.

5. The method of claim 4, wherein the virus comprises human flu virus.

6. The method of claim 1, wherein the light detector is a camera and where the camera receives light passing through a plurality of eggs in the carrier substantially simultaneously.

7. The method of claim 1, wherein the light source is a S Beam light candling system.

8. The method of claim 1, wherein the output signal corresponds to light based upon the outputs of a single, or group of, pixels received at a light detector for each respective egg.

9. The method of claim 1, wherein setting a first cutoff light level value and a second cutoff light level value comprises setting the first cutoff light level value between a peak of the rotten egg distribution profile and a peak of the live egg distribution profile.

10. The method of claim 9, wherein setting a first cutoff light level value and a second cutoff light level value comprises setting the second cutoff light level value between the peak of the live egg distribution profile and a peak of the dead egg distribution profile.

11. The method of claim 9, wherein the rotten egg distribution profile and the live egg distribution profile overlap, and the first cutoff light level value is set so as to include at least a portion of the rotten egg distribution profile when designating eggs as live eggs.

12. An apparatus that identifies live eggs, comprising:
   a candler that candles eggs within a carrier, the candler comprising:
   a light source that illuminates each egg within a carrier with light; and
   a detector that receives light passing through each egg from the light source and that generates an output signal corresponding to the received light; and
   a processor in communication with the candler that analyzes the output signal for each egg to determine and store a light level value of each egg, wherein the processor designates each egg as one of live and non-live according to an egg opacity level distribution profile having a plurality of egg status distribution profiles indicative of egg viability at day eleven of incubation, the plurality of egg status distribution profiles comprise a rotten egg distribution profile, a live egg distribution profile, a dead egg distribution profile, and an infertile egg distribution profile, wherein each distribution profile corresponds to a different light level value range, and further wherein the processor designates an egg as non-live if the light level value is less than a first cutoff light level value as set according to the egg opacity level distribution profile, and further wherein the processor designates an egg as non-live if the light level value is greater than a second cutoff light level value as set according to the egg opacity level distribution profile, the second cutoff light level being greater than the first cutoff light level value such that eggs analyzed as having light level values ranging between the first and second cutoff light level values are designated as live eggs.

13. The apparatus of claim 12, further comprising an egg removal device that removes eggs from the carrier.

14. The apparatus of claim 13, wherein the egg removal device removes non-live eggs from the carrier.

15. The apparatus of claim 13, further comprising a backfill station that replaces non-live eggs removed from the carrier with eggs prior to subsequent processing.

16. The apparatus of claim 12, further comprising an injection device configured to inject a substance into each live egg.

17. The apparatus of claim 16, wherein the substance comprises a virus.

18. The apparatus of claim 17, wherein the virus comprises human flu virus.

19. The apparatus of claim 12, wherein the detector comprises a photodetector.

20. The apparatus of claim 12, wherein the detector is a video camera.

21. The apparatus of claim 20, wherein the video camera receives light passing through a plurality of eggs in the carrier substantially simultaneously.

22. The apparatus of claim 12, wherein the first cutoff light level value is set between a peak of the rotten egg distribution profile and a peak of the live egg distribution profile.

23. The apparatus of claim 22, wherein the second cutoff light level value is set between the peak of the live egg distribution profile and a peak of the dead egg distribution profile.

24. The apparatus of claim 22, wherein the rotten egg distribution profile and the live egg distribution profile overlap, and the first cutoff light level value is set so as to include at least a portion of the rotten egg distribution profile when designating eggs as live eggs.

* * * * *